(12) United States Patent
Blom et al.

(10) Patent No.: US 10,413,399 B2
(45) Date of Patent: Sep. 17, 2019

(54) MEDICAL DEVICE INSERTION METHOD AND APPARATUS

(71) Applicant: HANSA MEDICAL PRODUCTS, INC., Carmel, IN (US)

(72) Inventors: Eric D. Blom, Carmel, IN (US); Brian Kamradt, Indianapolis, IN (US)

(73) Assignee: HANSA MEDICAL PRODUCTS, INC., Carmel, IN (US)

(*) Notice: Subject to any disclaimer, the term of this patent is extended or adjusted under 35 U.S.C. 154(b) by 119 days.

(21) Appl. No.: 14/996,535

(22) Filed: Jan. 15, 2016

(65) Prior Publication Data

US 2016/0206422 A1     Jul. 21, 2016

Related U.S. Application Data

(60) Provisional application No. 62/103,833, filed on Jan. 15, 2015.

(51) Int. Cl.
*A61F 2/20* (2006.01)

(52) U.S. Cl.
CPC .............. *A61F 2/20* (2013.01); *A61F 2/203* (2013.01); *A61F 2210/009* (2013.01)

(58) Field of Classification Search
USPC .................................. 623/9, 11; 606/75, 300
See application file for complete search history.

(56) References Cited

U.S. PATENT DOCUMENTS

| | | | |
|---|---|---|---|
| 4,245,358 A | 1/1981 | Moasser | |
| 4,435,853 A | 3/1984 | Blom et al. | |
| 4,586,931 A | 5/1986 | Blom et al. | |
| 4,614,516 A | 9/1986 | Blom et al. | |
| 4,636,205 A | 1/1987 | Steer | |
| 4,773,412 A | 9/1988 | Blom | |
| 4,911,716 A | 3/1990 | Blom et al. | |
| 5,064,433 A | 11/1991 | Blom et al. | |
| 5,294,917 A * | 3/1994 | Wilkins | G01F 23/38 |
| | | | 200/84 C |
| 5,300,119 A | 4/1994 | Blom | |
| 5,507,809 A | 4/1996 | Blom | |
| 5,571,180 A | 11/1996 | Blom | |
| 5,919,231 A | 7/1999 | Blom et al. | |
| 5,957,978 A | 9/1999 | Blom | |
| 6,722,367 B1 | 4/2004 | Blom | |
| 6,776,797 B1 | 8/2004 | Blom et al. | |
| 7,025,784 B1 | 4/2006 | Blom et al. | |
| 7,166,128 B1 | 1/2007 | Persson | |

(Continued)

FOREIGN PATENT DOCUMENTS

DE     102004051679 B3     12/2005

OTHER PUBLICATIONS

International Search Report and Written Opinion, International Application No. PCT/US2016/013559, dated Mar. 3, 2016, 9 pages.

*Primary Examiner* — Yashita Sharma

(74) *Attorney, Agent, or Firm* — Barnes & Thornburg LLP

(57) ABSTRACT

A device for maintaining a tract through a tissue wall having a proximal side and a distal side. The device includes a body, a retainer adjacent an end of the body which will lie on the distal side in the use orientation, and a flange adjacent an end of the body which will lie on the proximal side in the use orientation. The retainer comprises a ferromagnetic material that responds to a magnetic field to maintain the retainer in an undeployed, insertion orientation.

6 Claims, 17 Drawing Sheets

(56) References Cited

U.S. PATENT DOCUMENTS

| | | |
|---|---|---|
| RE39,923 E | 11/2007 | Blom |
| RE41,345 E | 5/2010 | Blom |
| 7,856,983 B2 | 12/2010 | Blom |
| 7,909,868 B2 | 3/2011 | blom |
| 7,975,696 B2 | 7/2011 | Blom |
| 7,987,851 B2 | 8/2011 | Blom et al. |
| 8,696,697 B2 | 4/2014 | Blom et al. |
| 8,707,956 B2 | 4/2014 | Blom et al. |
| 8,784,487 B2 | 7/2014 | Blom et al. |
| 2004/0204759 A1 | 10/2004 | Blom et al. |
| 2007/0144526 A1 | 6/2007 | Blom et al. |
| 2008/0234682 A1* | 9/2008 | Park ............... A61B 17/0401 606/75 |
| 2009/0036983 A1 | 2/2009 | Tran |
| 2009/0095302 A1 | 4/2009 | Blom |
| 2009/0235936 A1 | 9/2009 | Blom |
| 2009/0259309 A1 | 10/2009 | Blom |
| 2009/0259310 A1 | 10/2009 | Blom |
| 2011/0011406 A1 | 1/2011 | Blom et al. |
| 2011/0093071 A1 | 4/2011 | Blom |
| 2012/0046690 A1 | 2/2012 | Blom |
| 2012/0172936 A1* | 7/2012 | Horrell ............ A61B 17/0401 606/319 |
| 2012/0215306 A1 | 8/2012 | Fagan et al. |
| 2013/0098358 A1 | 4/2013 | Blom et al. |
| 2013/0274634 A1 | 10/2013 | Blom et al. |
| 2013/0274876 A1 | 10/2013 | Blom et al. |
| 2014/0031951 A1 | 1/2014 | Costello et al. |

\* cited by examiner

MEDICAL DEVICE INSERTION METHOD AND APPARATUS

CROSS-REFERENCE TO RELATED APPLICATIONS

This application claims priority under 35 U.S.C. § 119 to U.S. Provisional Patent Application Ser. No. 62/103,833 entitled "MEDICAL DEVICE INSERTION METHOD AND DEVICE," which was filed on Jan. 15, 2015 and is hereby incorporated by reference.

BACKGROUND

Various types of flange- or wing-retained medical devices and methods are known. There are, for example, the devices and methods illustrated and described in U.S. Pat. Nos. 4,435,853; 4,614,516; 5,064,433; 5,300,119; 5,507,809; 5,571,180; 5,919,231; 6,776,797; RE39,923; 7,909,868; 7,975,696; 8,696,697; 8,784,487; and, the devices and methods illustrated and described in U.S. patent publications: 2004/0204759; 2007/0144526; 2009/0259309; 2009/0259310; 2011/0093071; 2012/0046690; 2013/0274634; 2013/274876, and references cited in these.

There are also the devices and methods illustrated and described in U.S. Pat. Nos. 4,586,931; 4,773,412; 4,911,716; 5,957,978; 6,722,367; 7,025,784; RE41,345; 7,856,983; 7,987,851; 8,707,956; and, the devices and methods illustrated and described in U.S. patent publications: 2009/0095302; 2009/0235936; 2011/0011406; 2013/0098358, and references cited in these.

The disclosures of these references are hereby incorporated herein by reference. This listing is not intended as a representation that a complete search of all relevant prior art has been conducted, or that no better references than those listed exist. Nor should any such representation be inferred.

SUMMARY

According to an aspect of the disclosure, a device is provided for maintaining a tract through a tissue wall having a proximal side and a distal side is disclosed. The device includes a body, a retainer adjacent an end of the body which will lie on the distal side in the use orientation, and a flange adjacent an end of the body which will lie on the proximal side in the use orientation. The retainer comprises a ferromagnetic material that responds to a magnetic field to maintain the retainer in an undeployed, insertion orientation.

According to another aspect, a voice prosthesis device is provided for a tracheoesophageal puncture. The voice prosthesis device includes a body, a retainer adjacent an esophageal end of the body, and a flange adjacent a tracheal end of the body. The retainer extends adjacent the anterior wall of the esophagus when the prosthesis is in the use orientation in a tracheoesophageal wall. The flange extends adjacent a posterior wall of the trachea when the prosthesis is in the use orientation in a tracheoesophageal wall. The retainer comprises a ferromagnetic material that responds to a magnetic field to maintain the retainer in an undeployed, insertion orientation.

Illustratively according to these aspects, the retainer comprises a pair of wings adjacent the distal, or esophageal, end of the body, the wings projecting generally in opposite directions along the distal side, or anterior wall of the esophagus, when the prosthesis is in the use orientation in the wall.

Alternatively illustratively according to these aspects, the retainer comprises a flange adjacent the distal, or esophageal, end of the body, the flange projecting generally along the distal side, or anterior wall of the esophagus, when the prosthesis is in the use orientation in the wall.

Illustratively according to these aspects, the ferromagnetic material comprises at least one magnet.

Alternatively illustratively according to these aspects, the ferromagnetic material comprises a ferromagnetic coating.

Illustratively according to these aspects, the retainer comprises a filled resin or polymer. Further or alternatively according to these aspects, the ferromagnetic material comprises a ferromagnetic filler.

Further illustratively according to these aspects, the apparatus includes a stem for insertion through a passageway in the body and between the magnets to separate them.

Alternatively illustratively according to these aspects, the apparatus further includes a stem provided at a distal end with a magnet. The stem is adapted for insertion through a passageway in the body to hold the ferromagnetic material and thereby the retainer in an undeployed, insertion orientation.

According to another aspect, a prosthesis system comprises a prosthesis device. The prosthesis device comprises a body extending from a proximal end to a distal end. The body includes a longitudinal axis and a passageway extending through the body along the longitudinal axis, a first flange extending outwardly from the proximal end, a second flange extending from the distal end, and a pair of ferromagnetic elements attached to the second flange. The second flange is movable relative to the body between a first position in which the pair of ferromagnetic elements are proximate to one another and the longitudinal axis of the body, and a second position in which the ferromagnetic elements are positioned on opposite sides of the body.

Illustratively according to this aspect, each ferromagnetic element is a magnet.

Illustratively according to this aspect, the magnets cooperate to hold the second flange in the first position.

Alternatively illustratively according to this aspect, each ferromagnetic element is a ferromagnetic strip.

Alternatively illustratively according to this aspect, each ferromagnetic element includes ferromagnetic filler embedded in the second flange.

Further illustratively according to this aspect, the prosthesis system comprises a stem sized to be inserted into the passageway of the body. The stem includes a tip configured to engage the second flange to urge the second flange to move from the first position to the second position.

Further or alternatively illustratively according to this aspect, the prosthesis system comprises a stem sized to be inserted into the passageway of the body. The stem includes a magnet configured to attract the pair of ferromagnetic elements.

Further illustratively according to this aspect, the prosthesis system comprises a stem sized to be inserted into the passageway of the body. The stem includes a tip configured to engage the second flange and a magnet attached to the tip that is configured to attract the pair of ferromagnetic elements.

Illustratively according to this aspect, the tip of the stem is rotatable relative to the body between a first orientation in which the magnet faces the pair of ferromagnetic elements and a second orientation in which the magnet is turned away from the pair of ferromagnetic elements.

Illustratively according to this aspect, the body comprises a corrugated tube formed from an elastomeric material.

Illustratively according to this aspect, the second flange includes a pair of wings that project in opposite directions from the body when in the second position. One of the ferromagnetic elements is attached to each wing.

Illustratively according to this aspect, each wing extends from a base attached to the body to an outer tip, and one of the pair of ferromagnetic elements is attached to the outer tip of each wing.

Illustratively according to this aspect, the second flange is a somewhat disk-shaped flange extending from the body. The ferromagnetic elements are diametrically spaced apart when the second flange is in the second position.

Illustratively according to this aspect, the somewhat disk-shaped flange is circular when in the second position.

Illustratively according to this aspect, the body includes a valve positioned in the passageway.

Illustratively according to this aspect, the body, the first flange, and the second flange are formed from 50 to 60 Shore A durometer silicone.

Illustratively according to this aspect, the prosthesis system includes a pair of wires extending through the body and coupled to the second flange. The pair of wires are configured to be moved in a first direction to move the second flange from the second position to the first position.

According to another aspect, a prosthesis device comprises a body extending from a distal end to a proximal end. The body includes a longitudinal axis and a passageway extending through the body along the longitudinal axis, a flange extending outwardly from the proximal end, a first wing extending from the distal end, the first wing having a first magnet secured thereto, and a second wing extending from the distal end, the second wing having a second magnet secured thereto. The first wing and the second wing are movable relative to the body between a first position in which the first wing is engaged with the second wing, and a second position in which the first wing and the second wing extend in opposite directions from the body. The first magnet and the second magnet are configured to hold the first wing and the second wing in the first position.

According to another aspect, a prosthesis device comprises a body extending from a distal end to a proximal end. The body includes a longitudinal axis and a passageway extending through the body along the longitudinal axis, a first flange extending outwardly from the proximal end, and a second flange extending from the distal end. The second flange has a first magnet and a second magnet secured thereto. The second flange is movable relative to the body between a first position in which the first magnet is proximate to the second magnet and the longitudinal axis of the body, and a second position in which the first magnet is diametrically spaced apart from the second magnet.

According to another aspect, a method of using a voice prosthesis device comprises inserting a stem into a passageway defined in the voice prosthesis device that is implanted in a patient's tracheoesophageal puncture, grasping a proximal flange of the implanted voice prosthesis device to move the implanted voice prosthesis device anteriorly and draw a first wing of the voice prosthesis device toward a second wing of the voice prosthesis device, orienting the stem relative to a first magnet positioned in the first wing and a second magnet positioned in the second wing to attract the first wing and the second wing to the stem, and removing the voice prosthesis device and the stem from the patient's tracheoesophageal puncture with the first wing and the second wing engaged with the stem.

Illustratively according to this aspect, the method further comprises moving the first wing toward the second wing such that the first magnet and the second magnet draw the first wing into engagement with the second wing, inserting the voice prosthesis device into the patient's tracheoesophageal puncture with the first wing engaged with the second wing, and separating the first magnet and the second magnet to permit the first wing and the second wing to deploy outward and engage an anterior wall of the patient's esophagus.

Illustratively according to this aspect, separating the first magnet and the second magnet comprises inserting a stem into the passageway defined in the voice prosthesis device and advancing the stem between the first magnet and the second magnet.

According to another aspect, a method of using a voice prosthesis device, comprises inserting a stem into a passageway defined in a voice prosthesis device that is implanted in a patient's tracheoesophageal puncture, grasping a proximal flange of the implanted voice prosthesis device to move the implanted voice prosthesis device anteriorly and draw a first section of a distal flange of the voice prosthesis device toward a second section of the distal flange, orienting the stem relative to a first ferromagnetic element positioned in the first section of the distal flange and a second ferromagnetic element positioned in the second section of the distal flange to attract the first section and the second section of the distal flange to the stem, and removing the voice prosthesis device and the stem from the patient's tracheoesophageal puncture with the first section and the second section of the distal flange engaged with the stem.

According to another aspect, a prosthesis system comprising a prosthesis device is disclosed. The prosthesis device includes a body extending from a proximal end to a distal end. The body includes a longitudinal axis and a passageway extending through the body along the longitudinal axis. The prosthesis device also includes a flange extending outwardly from the proximal end and a first wing and a second wing extending from the distal end. The first wing and the second wing include ferromagnetic material. The first wing and the second wing are movable relative to the body between a first position in which the first wing is positioned proximate to the second wing and a second position in which the first wing and the second wing extend in opposite directions from the body.

Illustratively according to this aspect, the prosthesis system further comprises a stem sized to be inserted into the passageway of the body. The stem includes a magnet configured to attract the ferromagnetic materials in the first wing and the second wing to hold the first wing and the second wing in the first position.

Illustratively according to these aspects, the flange is a first flange, and the prosthesis device includes a second flange extending from the distal end such that the first wing and the second wing are positioned between the first flange and the second flange.

Illustratively according to these aspects, the prosthesis system further comprises a pair of wires extending through the body and coupled to the first wing and the second wing. The wires are configured to be moved in a first direction to move the first wing and the second wing from the second position to the first position.

According to another aspect, a method of using a voice prosthesis device comprises inserting a stem into a passageway defined in the voice prosthesis device that is implanted in a patient's tracheoesophageal puncture and drawing a first wing of the voice prosthesis device toward a second wing of the voice prosthesis device. The first wing and the second wing include ferromagnetic materials, and the method includes orienting the stem relative to the first wing and the second wing to attract the first wing and the second wing to the stem. The method also includes removing the voice prosthesis device and the stem from the patient's tracheoesophageal puncture with the first wing and the second wing engaged with the stem.

Illustratively according to this aspect, the ferromagnetic materials in the first wing and the second wing include a first magnet positioned in the first wing and a second magnet positioned in the second wing.

Illustratively according to these aspects, drawing the first wing of the voice prosthesis device toward the second wing of the voice prosthesis device includes pulling a pair of wires connected to the first wing and the second wing.

According to another aspect, a method of may include actuating the pair of magnets mounted on the stem to advance the magnets into engagement with the first wing and the second wing of the voice prosthesis device.

In some embodiments, actuating the pair of magnets may include advancing teeth formed on an actuator rod of the stem along teeth formed on each magnet to cause the magnets to rotate outward.

According to another aspect, a prosthesis system comprises a prosthesis device. The prosthesis device comprises a body extending from a proximal end to a distal end. The body includes a longitudinal axis and a passageway extending through the body along the longitudinal axis. A proximal flange extends outwardly from the proximal end, a pair of distal flanges extend from the distal end, and a ferromagnetic element is attached to each distal flange. Each distal flange is movable relative to the body between a first position in which the ferromagnetic elements are proximate to one another and the longitudinal axis of the body, and a second position in which the ferromagnetic elements are positioned on opposite sides of the body.

In some embodiments, the prosthesis system may include an insert sized to be positioned in the passageway of the prosthesis device. Additionally, in some embodiments, the insert may include an elongated body sized to be received in the passageway and a flange extending outwardly from the elongated body that is configured to engage the proximal flange of the prosthesis device when the elongated body is received in the passageway. In some embodiments, the insert may include a passageway extending along its longitudinal axis between a pair of open ends.

In some embodiments, the prosthesis system may further include a stem sized to be inserted into the passageway of the prosthesis device. The stem may include a ferromagnetic element configured to interact with the ferromagnetic elements in the distal flanges to hold the distal flanges in the first position.

In some embodiments, the ferromagnetic element of each distal flange includes a magnet. configured to attract the ferromagnetic element of the stem. Additionally, in some embodiments, the ferromagnetic element of the stem may include a magnet configured to attract the ferromagnetic elements of the distal flanges.

In some embodiments, the stem may include an elongated body, and the ferromagnetic element of the stem may include a first section movable relative to the elongated body and a second section movable relative to the elongated body. Additionally, in some embodiments, stem may include an actuator rod positioned in the elongated body that is configured to move the first section and the second section between an extended position and a retracted position.

In some embodiments, each of the actuator rod, the first section, and the second section include a plurality of teeth, the teeth of the actuator rod being engaged with the teeth of the first section and the teeth of the second section such that movement of the actuator rod along a longitudinal axis causes the first section and the second section to move between the extended position and the retracted position. Additionally, in some embodiments, the first section and the second section extend orthogonal to the longitudinal axis when in the extended position and extend parallel to the longitudinal axis when the retracted position.

In some embodiments, the body of the prosthesis device comprises a corrugated tube formed from an elastomeric material. In some embodiments, the body, the proximal flange, and the distal flanges are formed from 50 to 60 Shore A durometer silicone.

These flanged or winged devices find particular utility in obstructive sleep apnea or other airways applications, gastrostomy, otology and like applications.

BRIEF DESCRIPTION OF THE DRAWINGS

The detailed description particularly refers to the following figures, in which.

DETAILED DESCRIPTION OF THE DRAWINGS

Figure 1:
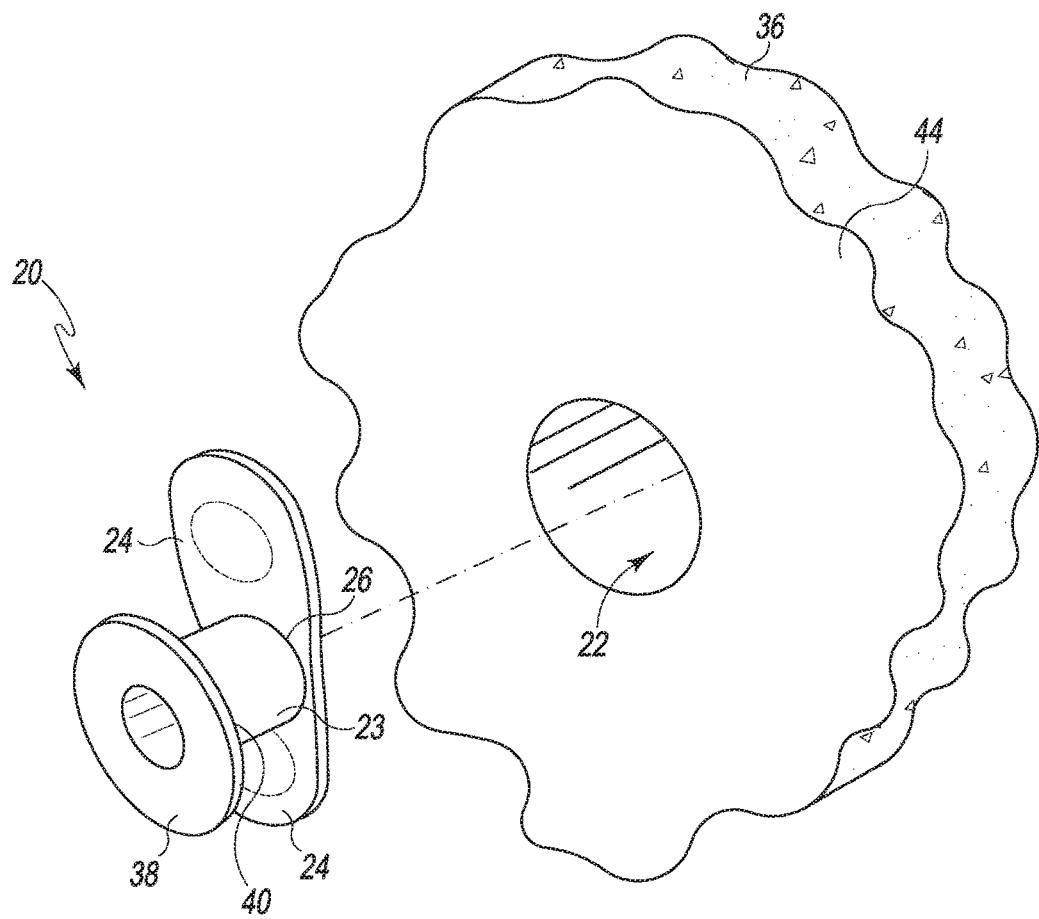
FIG. 1 illustrates a perspective view of a voice prosthesis device for use in a tracheoesophageal puncture in a patient.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIGS. 1-6, a voice prosthesis device 20 for a tissue puncture such as, for example, a tracheoesophageal puncture 22 is illustrated. Although the device 20 is shown in reference to use in a tracheoesophageal puncture, it should be appreciated that the device 20 may be used in other tissue puncture such as, for example, a puncture through a patient skin that opens into a patient's trachea. Device 20 is, for example, molded from a biocompatible material, such as a relatively low durometer silicone. The voice prosthesis device 20 is provided with a pair of wings 24 on the inner or esophageal end 26 of the prosthesis body 23. The wings 24 project in opposite directions along the anterior wall 28 of the esophagus 30 when the prosthesis 20 is in the use orientation in the tracheoesophageal wall 36. The flange 38 at the tracheal end 40 of the body 23 lies at the posterior wall 44 of the trachea 48. In this way, the body 23, and thus the entire prosthesis, is held in place in the tracheoesophageal wall 36.

Figure 2:
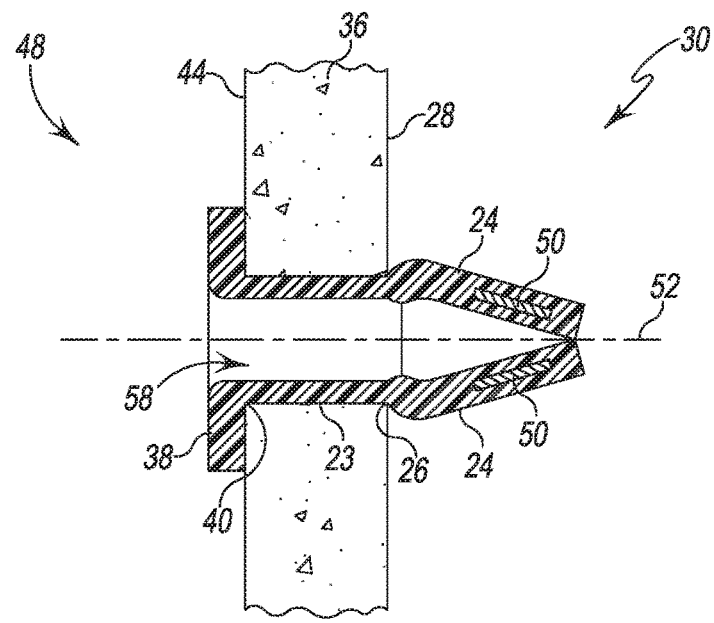
FIG. 2 illustrates a cross-sectional side elevation view illustrating the voice prosthesis device of FIG. 1 positioned in a tracheoesophageal puncture in a patient.
Figure 3:
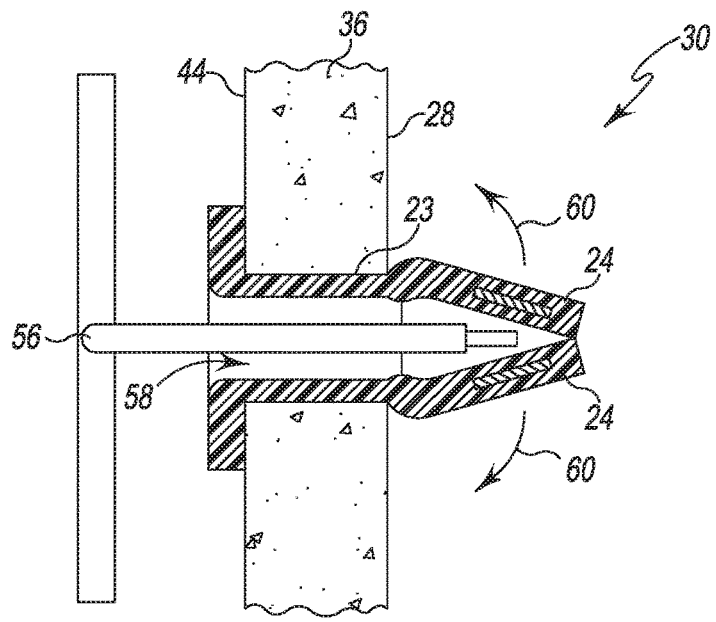
FIG. 3 is a view similar to FIG. 2 illustrating the voice prosthesis device of FIG. 1 positioned in the tracheoesophageal puncture in a patient.
Figure 4:
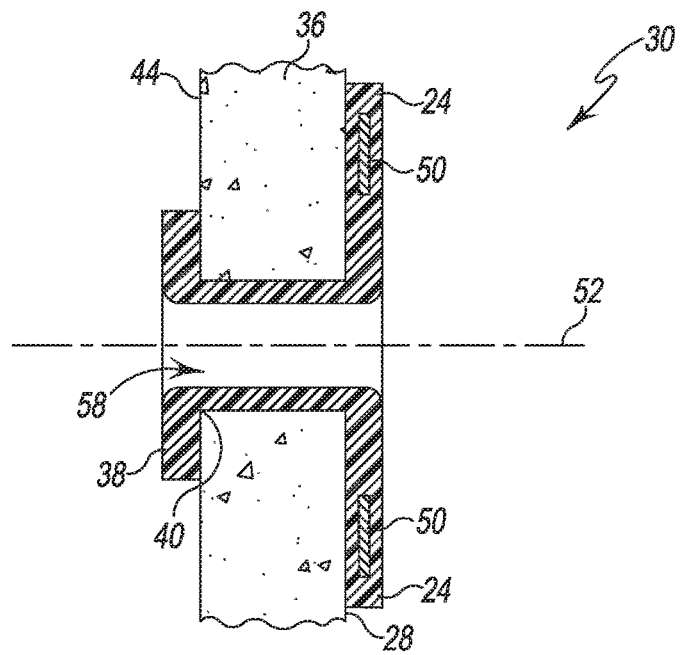
FIG. 4 is another view similar to FIGS. 2-3 illustrating the voice prosthesis device of FIG. 1 positioned in the tracheoesophageal puncture in a patient.

To facilitate insertion of the prosthesis 20 through the tracheoesophageal wall 36, each wing 24 is provided with a small magnet 50. Prior to insertion of the wings 24 through the puncture 22, the magnets 50 are brought together along the center line or axis 52. As illustrated in FIG. 2, the magnets 50 hold the wings 24 in this orientation while the wings 24 are threaded through the puncture 22 into the esophagus 30. Then, as illustrated in FIG. 3, a stem 56 is inserted through the passageway 58 in the body 23 and between the magnets 50, separating them and permitting the wings 24 to deploy as indicated in FIG. 3 by the arrows 60 into their use orientations against the anterior wall 28 of the esophagus 30, as illustrated in FIG. 4

Figure 5:
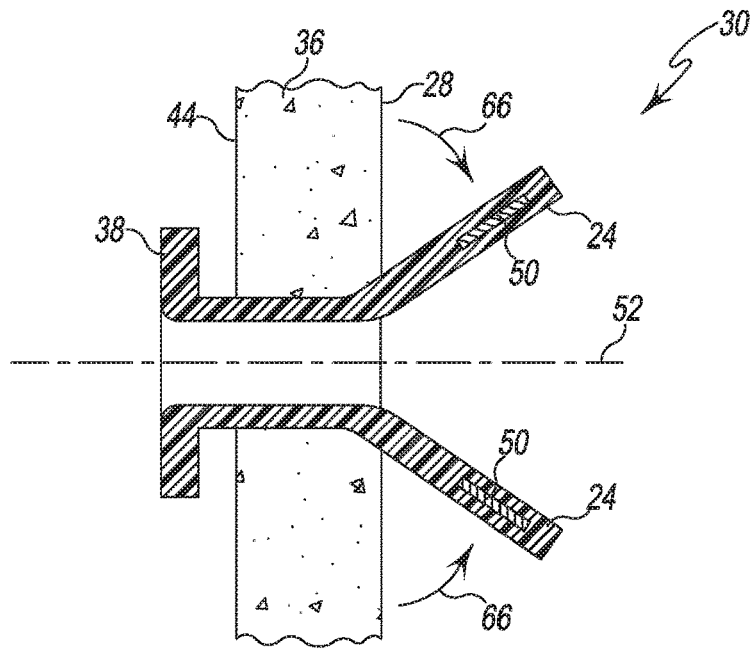
FIG. 5 is another view similar to FIGS. 2-4 illustrating the voice prosthesis device of FIG. 1 as it is being removed from the tracheoesophageal puncture in a patient.
Figure 6:
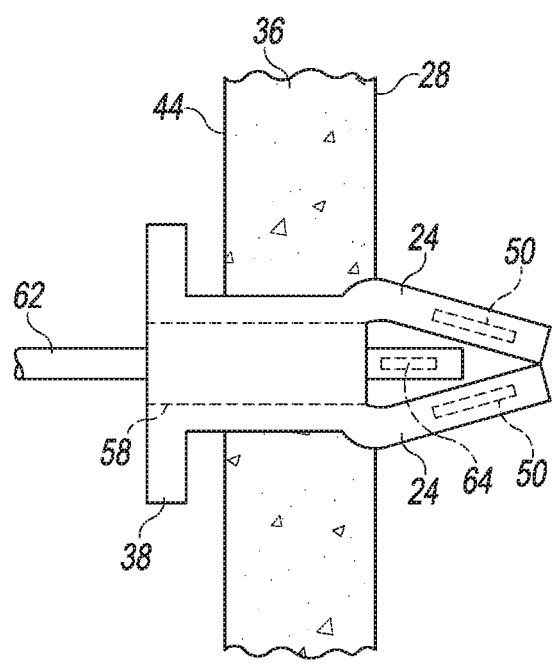
FIG. 6 is another view similar to FIG. 5 illustrating the voice prosthesis device of FIG. 1 as it is being removed from the tracheoesophageal puncture in a patient.

It is necessary from time to time to remove the prosthesis 20 for cleaning, replacement, or the like. As illustrated in FIG. 5, it may be helpful to pull gently on the flange 38 during the removal procedure so that contact with the tracheoesophageal wall 36 urges the wings 24 toward the centerline 52 of the body 23 as indicated by the arrows 66. In the removal procedure, another stem 62 having a magnet 64 at its distal end may be inserted through the passageway 58, as illustrated in FIG. 6. The magnet 64 on the end of the stem 62 also aids to pull the magnets 50, and thus the wings 24, toward each other, and into contact. It is easier with the wings 24 in this orientation to remove the prosthesis 20 from the tracheoesophageal wall 36.

Figure 7:
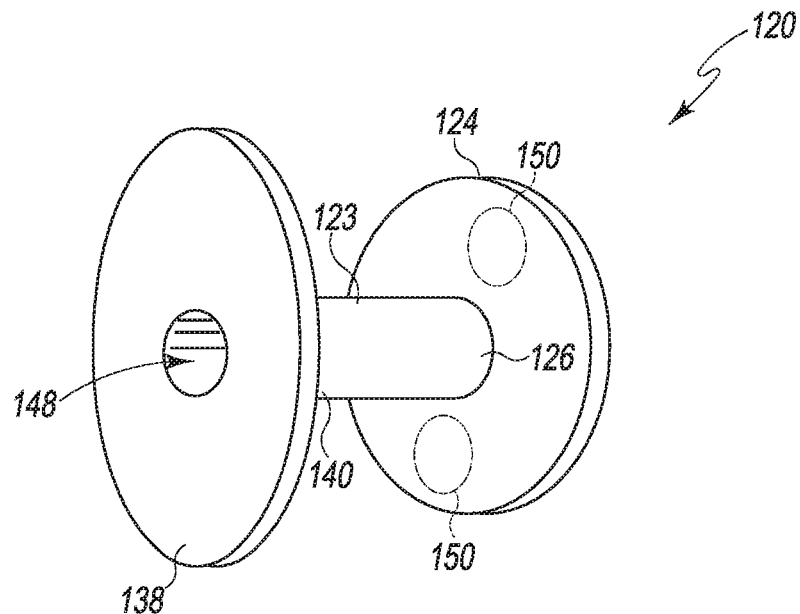
FIG. 7 illustrates a perspective view of another embodiment of a voice prosthesis device for use in a tracheoesophageal puncture in a patient illustrating the flange of the voice prosthesis device in a use orientation.
Figure 8:
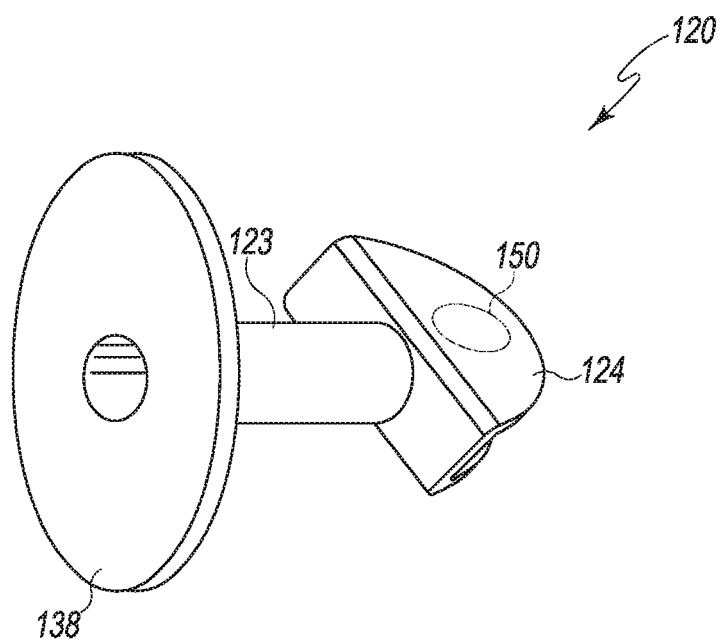
FIG. 8 is a view similar to FIG. 7 illustrating the flange of the voice prosthesis device in an insertion orientation.

Referring now to FIGS. 7-8, another embodiment of a voice prosthesis device 120 for a tracheoesophageal or other tissue puncture (not shown) is illustrated. The voice prosthesis device 120 is provided with a circular flange 124 on the esophageal end 126 of the prosthesis body 123. It should be appreciated that in other embodiments the flange 124 may be oval, rectangular, or other geometric shape. The flange 124 lies along the anterior wall 28 of the esophagus 30 when the prosthesis 120 is in the use orientation in the tracheoesophageal wall 36. Another oval flange 138 at the tracheal end 140 of the body 123 lies at the posterior wall 44 of the trachea 48. It should be appreciated that in other embodiments the flange 138 may be circular, rectangular, or other geometric shape. Additionally, the flanges 124, 138 may be the same shape. In this way, the body 123, and thus the entire prosthesis, is held in place in the tracheoesophageal wall 36.

To facilitate insertion of the prosthesis 120 through the tracheoesophageal wall 36, flange 124 is provided with two diametrically spaced small magnet 150. Prior to insertion of the flange 124 through the puncture (not shown), the magnets 150 are brought together as illustrated in FIG. 8. The magnets 150 hold the flange 124 in this orientation while the flange 124 is threaded through the puncture (not shown) into the esophagus 30. Then, a stem 56 is inserted through the passageway 158 in the body 123 and between the magnets 150, separating them and permitting the flange 124 to deploy into its use orientations against the anterior wall 28 of the esophagus 30.

Again, it is necessary from time to time to remove the prosthesis 120 for cleaning, replacement, or the like. In those circumstances, another stem 62 having a magnet 64 at its distal end is inserted through the passageway 158. During this procedure, it may be helpful to pull gently on the flange 138 so that contact with the tracheoesophageal wall 36 urges the magnets 150 toward the centerline of the body 123. The magnet 64 on the end of the stem 62 also aids to pull the magnets 150 toward each other, and into contact. It is easier with the flange 124 in this orientation to remove the prosthesis 120 from the tracheoesophageal wall 36.

Figure 9:
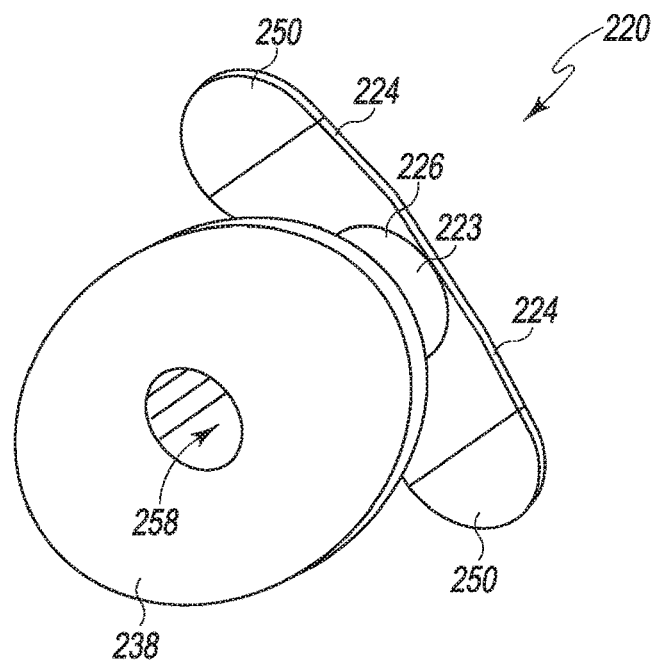
FIG. 9 illustrates a perspective view of another embodiment of a voice prosthesis device.
Figure 10:
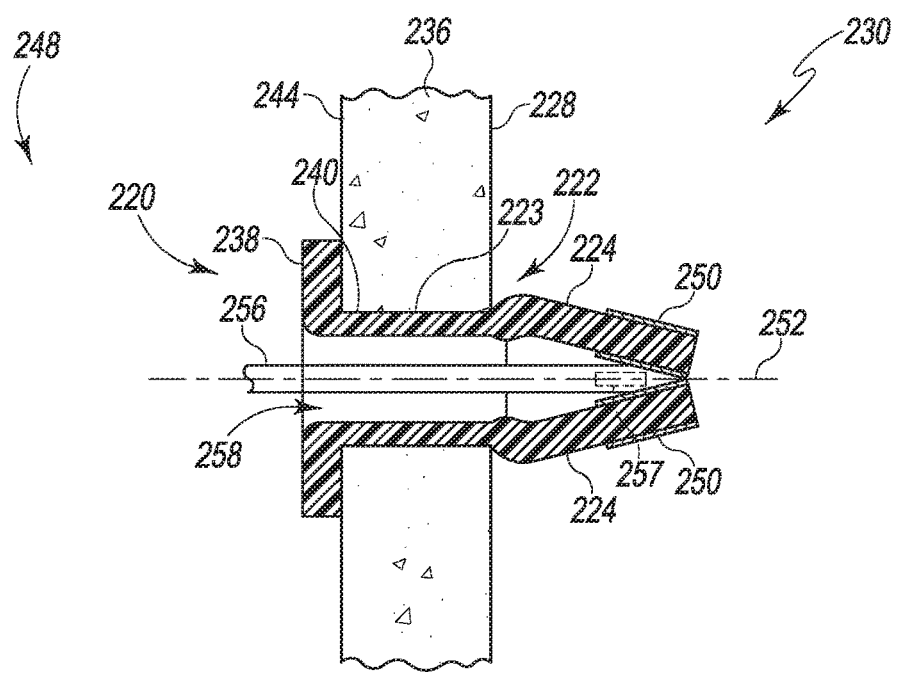
FIG. 10 illustrates a cross-sectional side elevation view of the voice prosthesis device of FIG. 9 positioned in a tracheoesophageal puncture in a patient.

Referring now to FIGS. 9-10, another embodiment of a voice prosthesis device 220 for a tracheoesophageal puncture 222 is illustrated. The voice prosthesis device 220 is provided with a pair of wings 224 on the esophageal end 226 of the prosthesis body 223. The wings 224 project in opposite directions along the anterior wall 228 of the esophagus 230 when the prosthesis 220 is in the use orientation in the tracheoesophageal wall 236. The flange 238 at the tracheal end 240 of the body 223 lies at the posterior wall 244 of the trachea 248. In this way, the body 223, and thus the entire prosthesis, is held in place in the tracheoesophageal wall 236.

To facilitate insertion of the prosthesis 220 through the tracheoesophageal wall 236, each wing 224 is provided with a strip of ferromagnetic material or strip of ferromagnetic coating 250. Prior to insertion of the wings 224 through the puncture 222, a stem 256 provided at its distal end with a magnet 257 is inserted through the passageway 258 in the body 223 and between the ferromagnetic strips 250, bringing the wings 224 into contact with the magnet 257 along the centerline 252. The magnet 257 holds the wings 224 in this orientation while the wings 224 are threaded through the puncture 222 into the esophagus 230. The stem 256 is then turned slightly causing the magnet 257 to release the ferromagnetic strips 250, permitting the wings 224 to deploy into their use orientations against the anterior wall 228 of the esophagus 230.

If it is necessary to remove the prosthesis 220 for cleaning, replacement, or the like, stem 256 can be reinserted through the passageway 258. Again, it may be helpful to pull gently on the flange 238 so that contact with the tracheoesophageal wall 236 urges the wings 224 toward the centerline of the body 223. The magnet 257 attracts the ferromagnetic strips 250, and thus the wings 224, into contact. It is easier with the wings 224 in this orientation to remove the prosthesis 220 from the tracheoesophageal wall 236.

Figure 11:
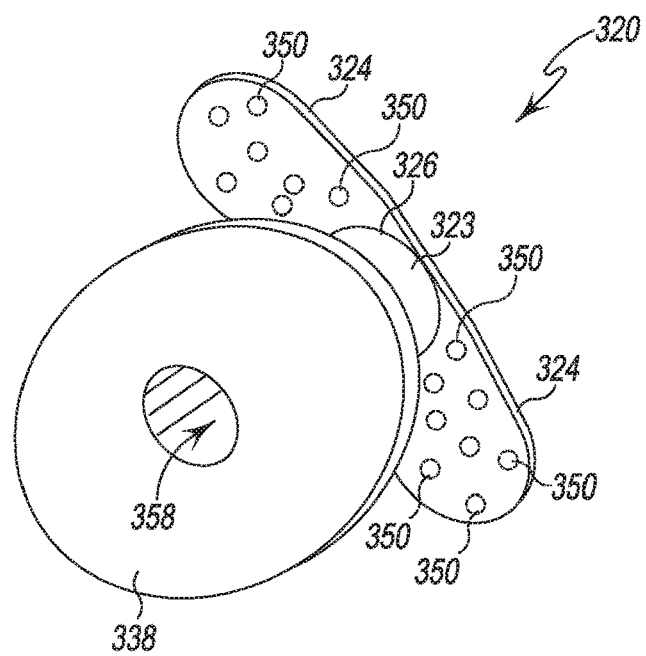
FIG. 11 illustrates a perspective view of another embodiment of a voice prosthesis device.
Figure 12:
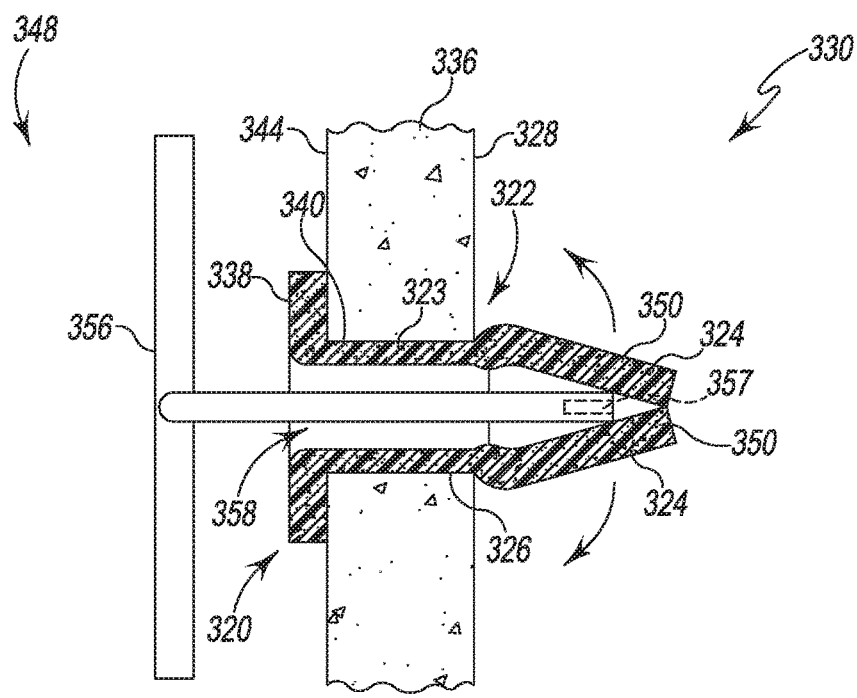
FIG. 12 illustrates a cross-sectional side elevation view of the voice prosthesis device of FIG. 11 positioned in a tracheoesophageal puncture in a patient.

Referring now to FIGS. 11-12, a voice prosthesis device 320 for a tracheoesophageal or other tissue puncture 322 is provided with a pair of wings 324 on the esophageal end 326 of the prosthesis body 323. The wings 324 project in opposite directions along the anterior wall 328 of the esophagus 330 when the prosthesis 320 is in the use orientation in the tracheoesophageal wall 336. The flange 338 at the tracheal end 340 of the body 323 lies at the posterior wall 344 of the trachea 348. In this way, the body 323, and thus the entire prosthesis, is held in place in the tracheoesophageal wall 336.

To facilitate insertion of the prosthesis 320 through the tracheoesophageal wall 336, at least the wings 324 of the prosthesis 320 are constructed from resin or polymer filled with powdered ferromagnetic material 350, for example, during molding, of the prosthesis 320, so that the wings 324 exhibit ferromagnetic characteristics. Prior to insertion of the wings 324 through the puncture 322, a stem 356 provided at its distal end with a magnet 357 is inserted through the passageway 358 in the body 323 and between the ferromagnetic material 350-filled wings 324, and the wings 324 are brought into contact with the magnet 357. The magnet 357 holds the wings 324 in this orientation while the wings 324 are threaded through the puncture 322 into the esophagus 330. The stem 356 is then manipulated, for example, turned slightly, so that the magnet 357 releases the ferromagnetic material 350-filled wings 324, permitting the wings 324 to deploy into their use orientations against the anterior wall 328 of the esophagus 330. The stem 356 is then withdrawn from the prosthesis 320.

If it is necessary to remove the prosthesis 320 for cleaning, replacement, or the like, stem 356 can be reinserted through the passageway 358. Again, it may be helpful to pull gently on the flange 338 so that contact with the tracheoesophageal wall 336 urges the ferromagnetic material 350-filled wings 324 toward the centerline of the body 323. The magnet 357 attracts the ferromagnetic material 350-filled wings 324 into contact. It is easier with the wings 324 in this orientation to remove the prosthesis 320 from the tracheoesophageal wall 336.

Figure 13:
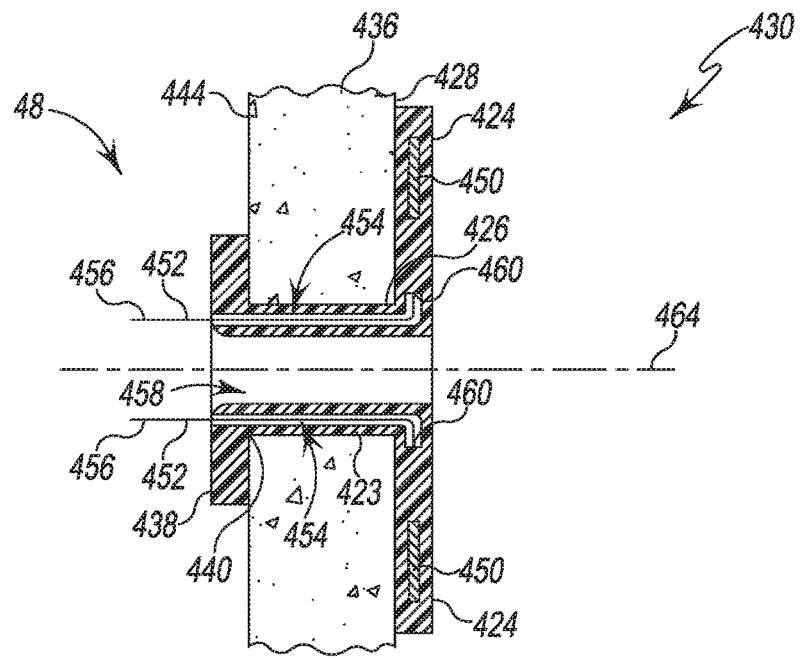
FIG. 13 illustrates a cross-sectional side elevation view of another embodiment of a voice prosthesis device positioned in a tracheoesophageal puncture in a patient.
Figure 14:
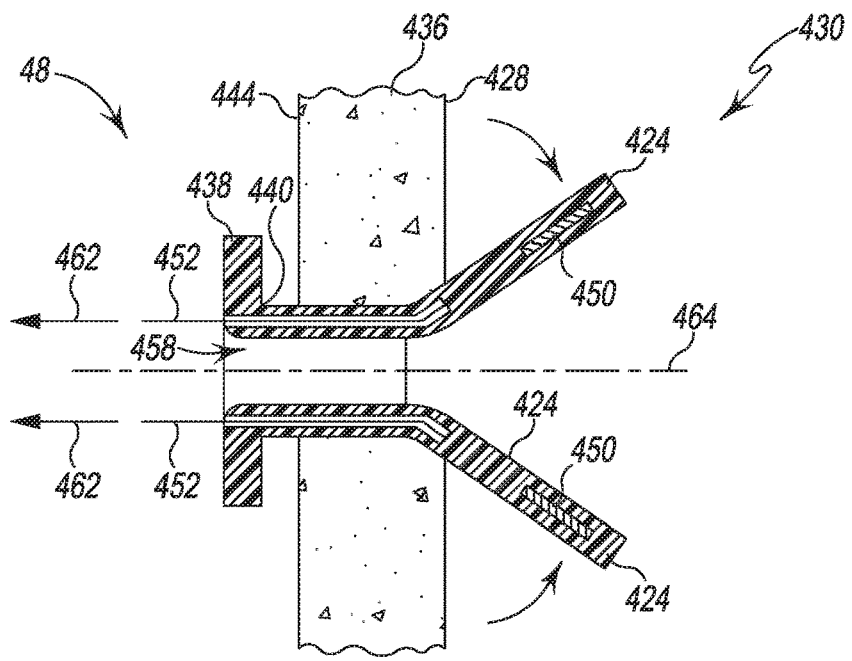
FIG. 14 is a view similar to FIG. 13 illustrating the voice prosthesis device as it is being removed from the tracheoesophageal puncture in a patient.

Referring now to FIGS. 13-14, a voice prosthesis device 420 for a tracheoesophageal or other tissue puncture 422 is provided with a pair of wings 424 on the esophageal end 426 of the prosthesis body 423. The wings 424 project in opposite directions along the anterior wall 428 of the esophagus 430 when the prosthesis 420 is in the use orientation in the tracheoesophageal wall 436 illustrated in FIG. 10. The flange 438 at the tracheal end 440 of the body 423 lies at the posterior wall 444 of the trachea 448. In this way, the body 423, and thus the entire prosthesis, is held in place in the tracheoesophageal wall 436.

To facilitate insertion of the prosthesis 420 through the tracheoesophageal wall 436, each wing 424 is provided with a small magnet 450. Prior to insertion of the wings 424 through the puncture 422, the magnets 450 are brought together. The magnets 450 hold the wings 424 in this orientation while the wings 424 are threaded through the puncture 422 into the esophagus 430. Then, a stem (not shown) may be inserted through the passageway 458 in the body 423 and between the magnets 450, separating them and permitting the wings 424 to deploy into their use orientations against the anterior wall 428 of the esophagus 430.

If it is necessary to remove the prosthesis 420 for cleaning, replacement, or the like, the prosthesis 420 includes a pair of pull-wires 452 that are positioned in passageways 454 defined in the body 423. As illustrated in FIGS. 13 and 14, each wire 452 has a proximal end 456 that extends outwardly from the body 423 and a distal end 460 attached to one of the wings 424. To remove the prosthesis 420, a user may pull on the proximal ends 456 of the wires 452 as indicated by the arrows 462 in FIG. 14 to urge the wings 424 toward the centerline 464 of the body 423. Another stem (not shown) having a magnet at its distal end may also be inserted through the passageway 458 to aid in pulling the magnets 450, and thus the wings 424, toward each other, and into contact. It is easier with the wings 424 in this orientation to remove the prosthesis 420 from the tracheoesophageal wall 436.

Figure 15:
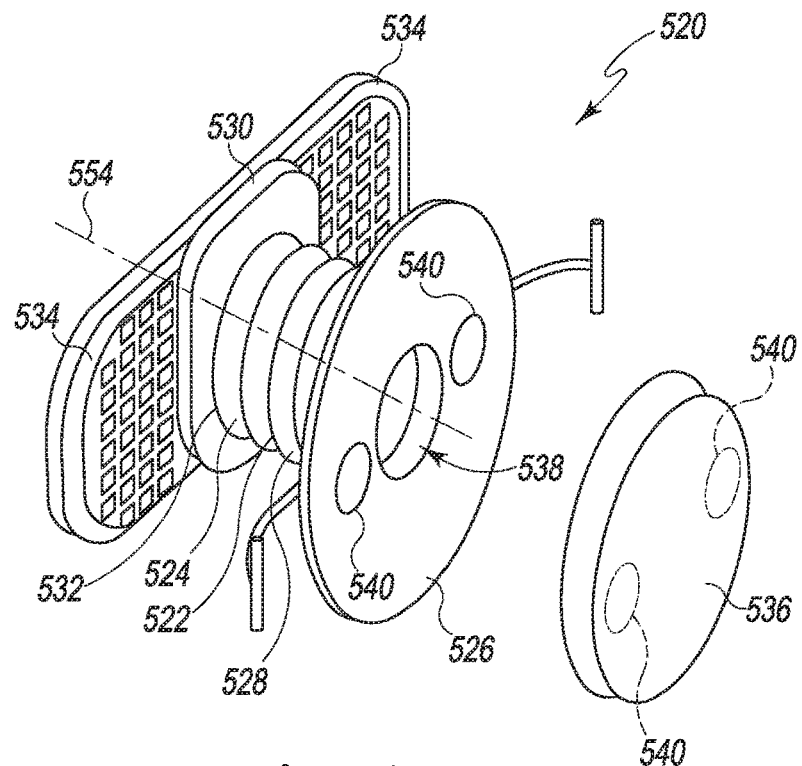
FIG. 15 is an exploded perspective view of a device for use in a tissue puncture in a patient.

Referring now to FIG. 15, a device 520 for use in a tracheostoma or other tissue puncture is illustrated. This device 520 may be used, for example, in the treatment of sleep apnea. The device 520 includes a body 522 that is a hollow tube constructed of a biocompatible elastomeric material such as, for example, silicone. The body 522 is sized to be positioned in a tissue puncture, and, in the illustrative embodiment, the body 522 includes a corrugated section 524 to permit the body 522 to increase or decrease in length as necessary during use.

The device 520 includes a flange 526 that extends outwardly from a proximal end 528 of the body 522 and another flange 530 that extends outwardly from an opposite distal end 532. The flange 526 is circular, and the flange 530 is square, but it should be appreciated that in other embodiments either or both of the flanges 526, 530 may be circular, oval, rectangular, or other geometric shape. Additionally, the flanges 526, 530 need not be the same shape. The flanges 526, 530 are illustratively molded integrally with the body 522. In other embodiments, one or more of the body 522 and the flanges 526, 530 may be formed separately and later assembled. In use, the flange 526 lies at the skin of the patient's neck when the body 522 is positioned in the tissue puncture, while the flange 530 lies along the anterior wall of the patient's trachea.

A pair of wings 534 are positioned adjacent to the distal end 532 of the body 522 and the flange 530. The wings 534 are configured to project in opposite directions along the anterior wall of a trachea when the device 520 is in a use orientation. When the wings 534 are deployed in the use orientation illustrated in FIGS. 15-16, the wings 534 cooperate with the flanges 526, 530 to hold the device 520 in place in the tissue puncture. Each wing 534 is formed from a ferromagnetic material such as thin sheets of ferromagnetic stainless steel or the like.

Figure 16:
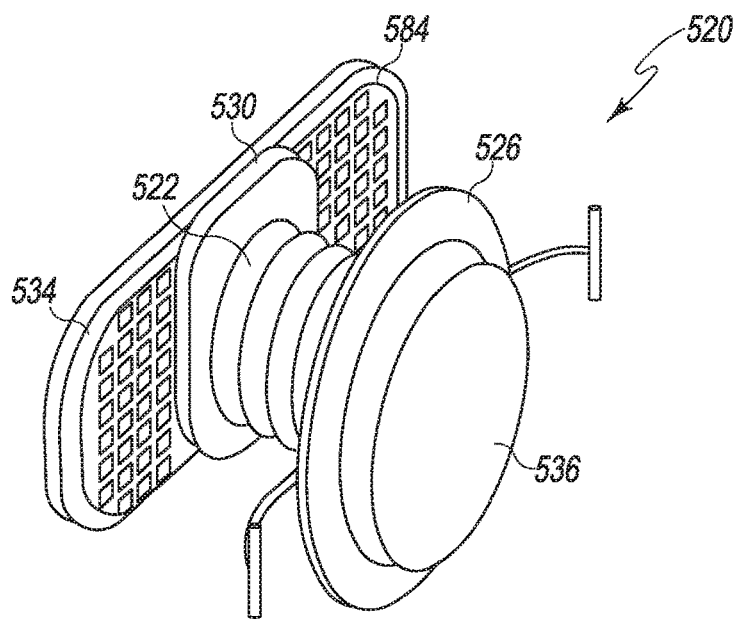
FIG. 16 is another perspective view of the device of FIG. 15.

As illustrated in FIGS. 15 and 16, the device 520 includes a cover 536 sized to be positioned over opening 538 of the body 522. The cover 536 is configured to selectively close the opening 538 to permit the patient to speak and breathe normally. The cover 536 may be removed at other times to permit air to pass directly into the trachea, thereby bypassing the throat. The cover 536 may be provided with a seal or gasket to facilitate the closure of the opening 538. To attach the cover 536 to the device 520 as illustrated in FIG. 16, the flange 526 is provided with magnets 540 and the cover 536 comprises ferromagnetic material so that it is attracted by the magnets 540 to secure the cover 536 in position over the opening 538.

Figure 17:
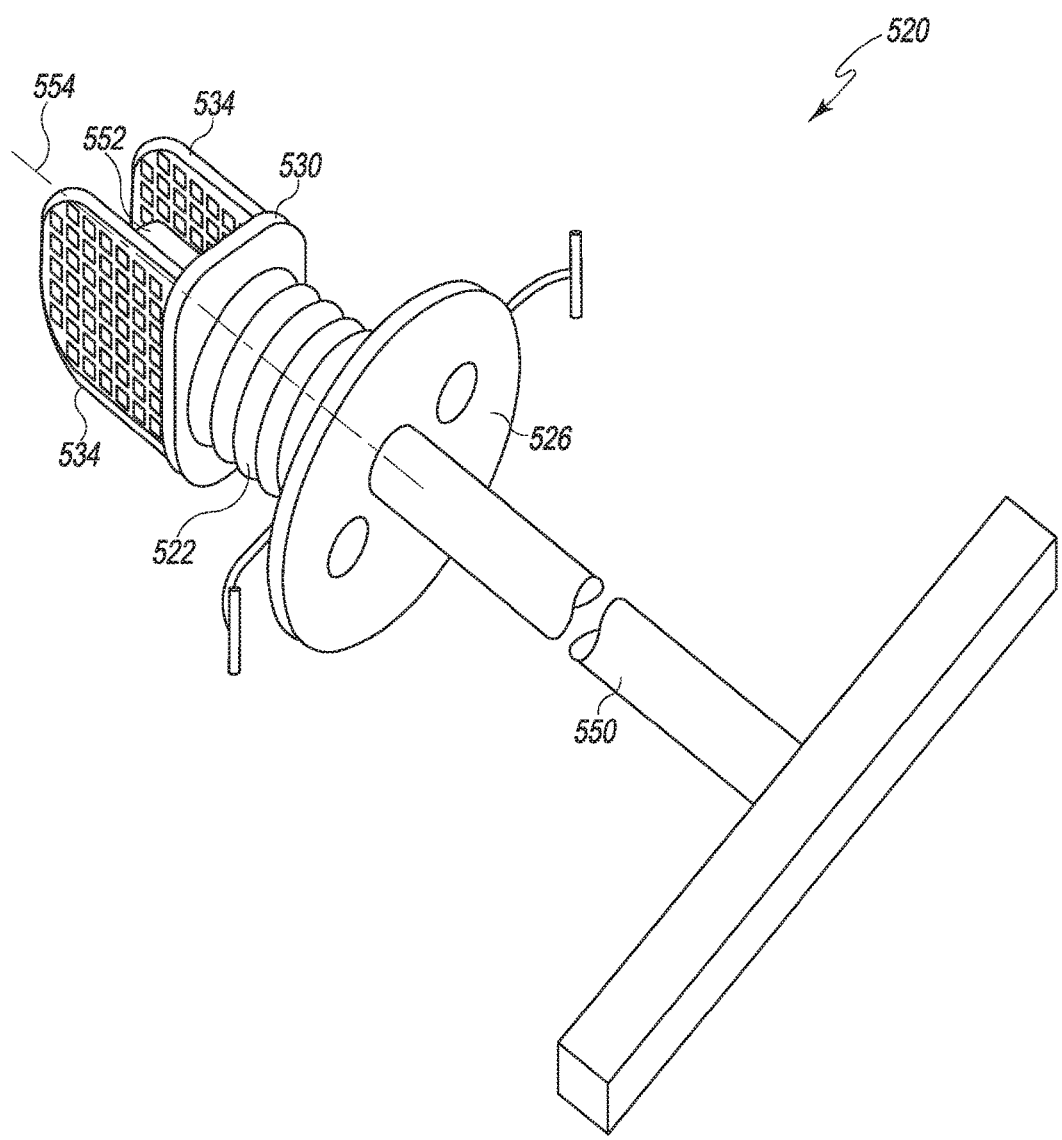
FIG. 17 is a perspective view showing the device of FIG. 15 in an insertion orientation.
Figure 18:
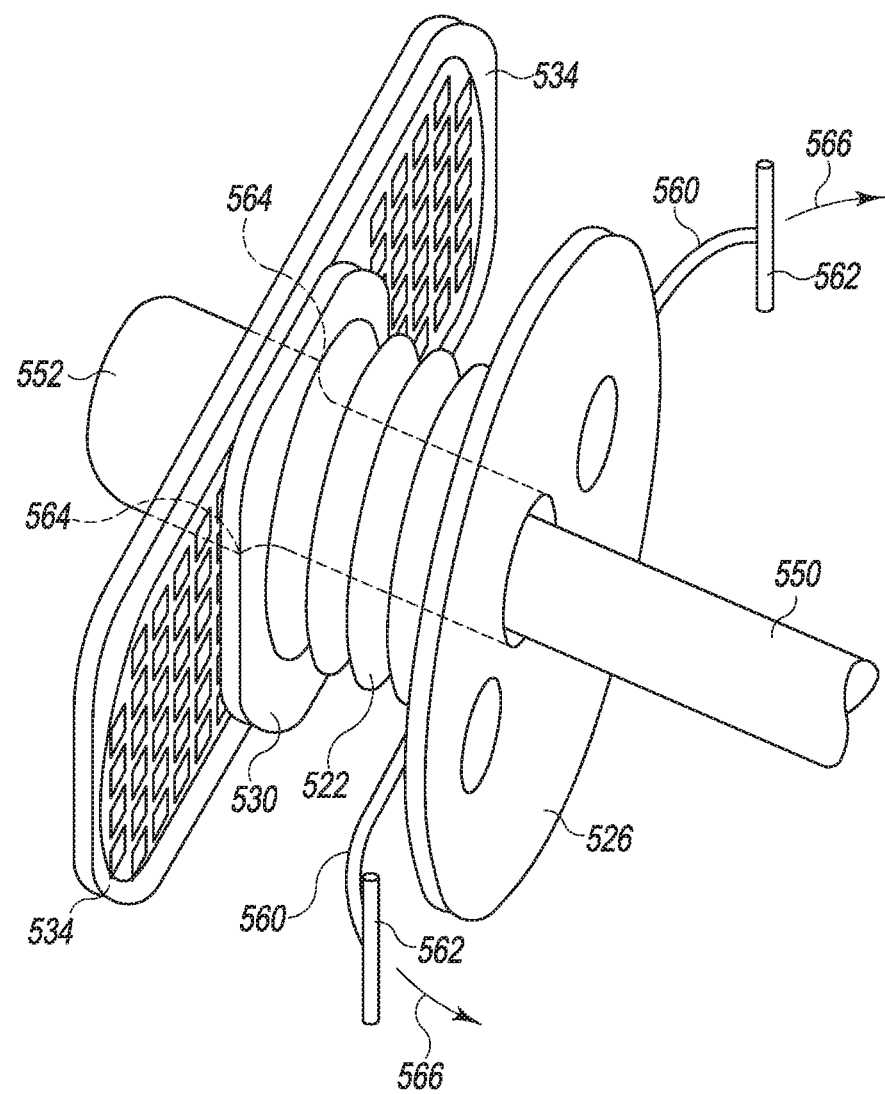
FIG. 18 is a perspective view showing the device of FIG. 15 in a use orientation.

Prior to insertion of the flange 530 and the wings 534 through the tissue puncture, a stem 550 is inserted through the body 522 between the wings 534, as illustrated in FIG. 17. The stem 550 is provided at its distal end with a magnet 552, and the wings 534 are folded into contact with the magnet 552 along the centerline 554 of the device 520. To facilitate insertion of the device 520 through tissue puncture, the magnet 552 holds the wings 534 and the flange 530 in this orientation while the wings 534 and the flange 530 are threaded through the tissue puncture into the trachea. The stem 550 may then be turned slightly, causing the magnet 552 to release the wings 534 and permitting the wings 534 to deploy into their use orientations, as illustrated in FIG. 18.

If it is necessary to remove the device 520 for cleaning, replacement, or the like, the device 520 includes a pair of pull-wires 560 that are positioned in passageways defined in the body 522. As illustrated in FIG. 18, each wire 560 has a handle end 562 that extends outwardly from the body 522 behind the flange 526 and another end 564 attached to one of the wings 534. To remove the device 520, a user may pull on the handle ends 562 of the wires 560 as indicated by the arrows 566 in FIG. 18 to urge the wings 534 toward the centerline of the body 522. The stem 550 may re-inserted into the body 522 to aid in pulling wings 534 toward each other, and into contact with the stem 550. It is easier with the wings 534 in this orientation to remove the device 520 from the tissue puncture.

Figure 19:
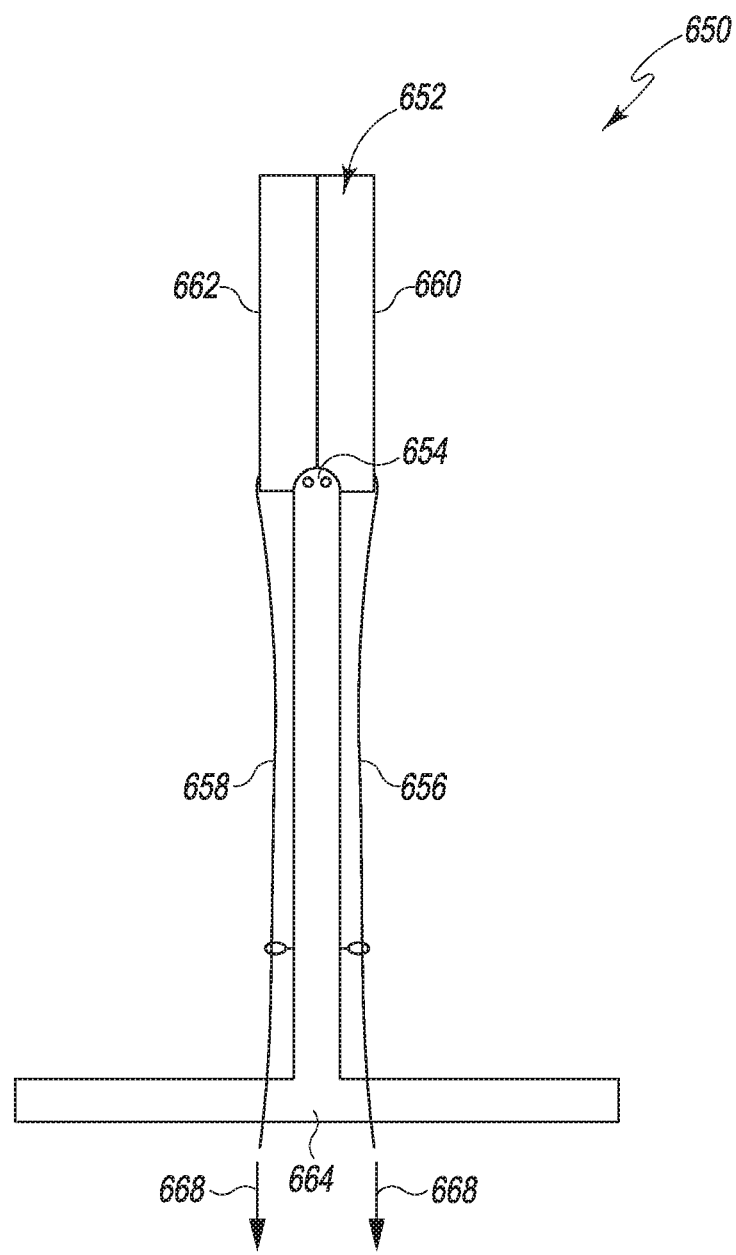
FIG. 19 is an elevation view of an insertion tool for use with any of the embodiments of FIGS. 1-18.
Figure 20:
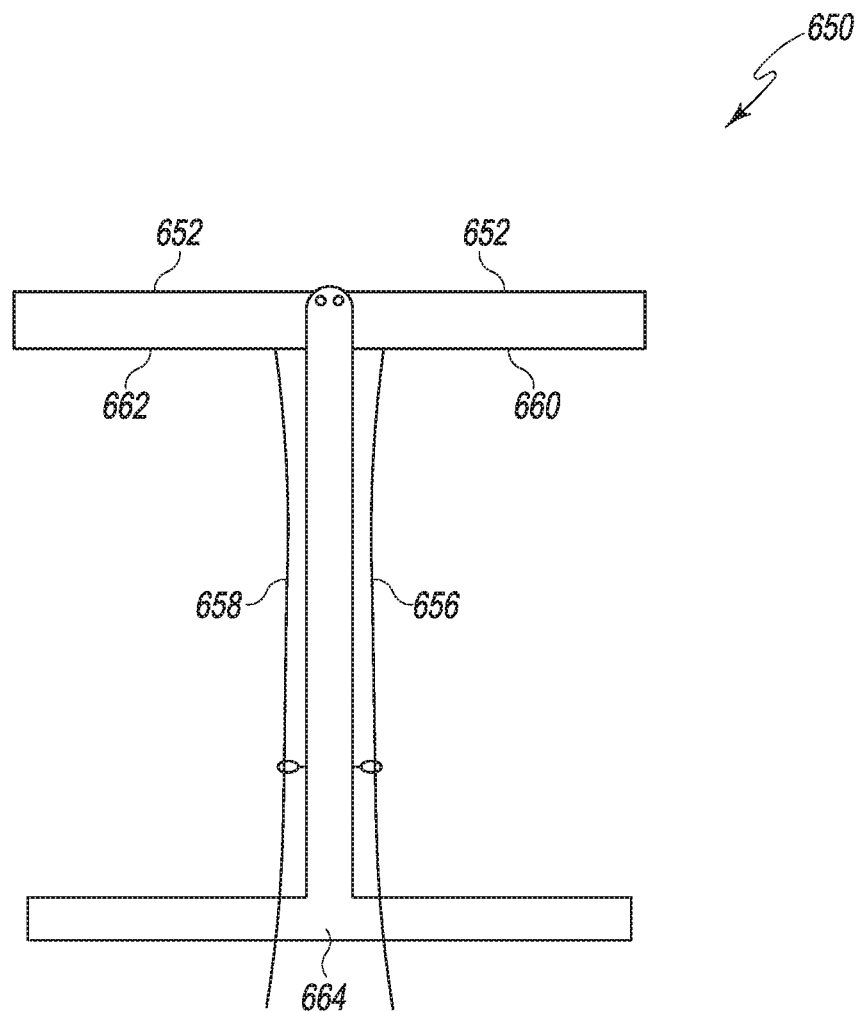
FIG. 20 is a view similar to FIG. 19 of the insertion tool.

Referring now to FIGS. 19-20, an insertion tool 650 for use with any of the embodiments described above is illustrated. The insertion tool 650 includes a magnet 652 that is hinged on its tip 654. The insertion tool 650 includes a pair of pull wires 656, 658, which are connected to a first face 660 and a second face 662, respectively, of the magnet 652. The pull wires 656, 658 extend to the proximal end 664 of the insertion tool 650. When the wires 656, 658 are pulled in the direction indicated by arrows 668, the magnet 652 folds over as shown in FIG. 20 to meet the magnets 50, 150, 450 or ferromagnetic materials 250, 350, 534 in the wings or flanges of the prosthesis devices 20, 120, 220, 320, 420, 520 when the wings or flanges are in the deployed or use orientation such that the wings or flanges can be pulled into the un-deployed position so that the prosthesis device may be removed from the tissue. The insertion tool 650 further includes a return spring, which biases the magnet 652 in the center position shown in FIG. 19, and returns the magnet 652 to its center position when a user stops pulling the wire.

Figure 21:
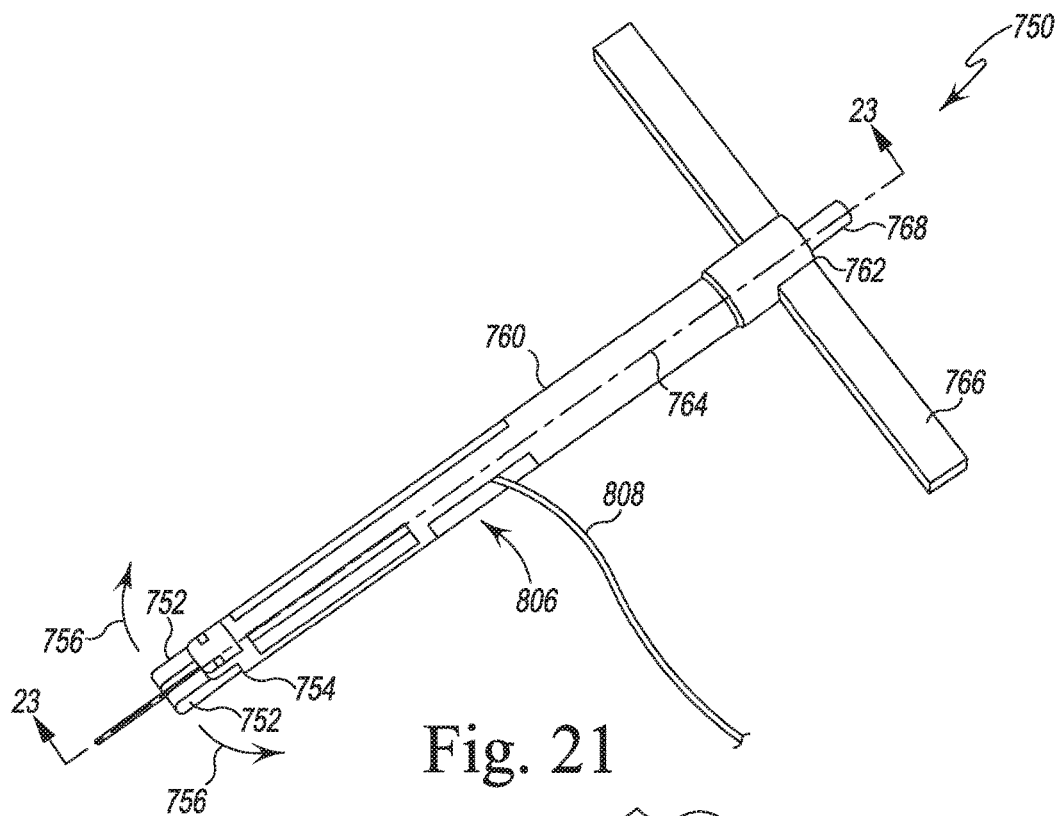
FIG. 21 is a perspective view of another insertion tool for use with any of the embodiments of FIGS. 1-18.
Figure 22:
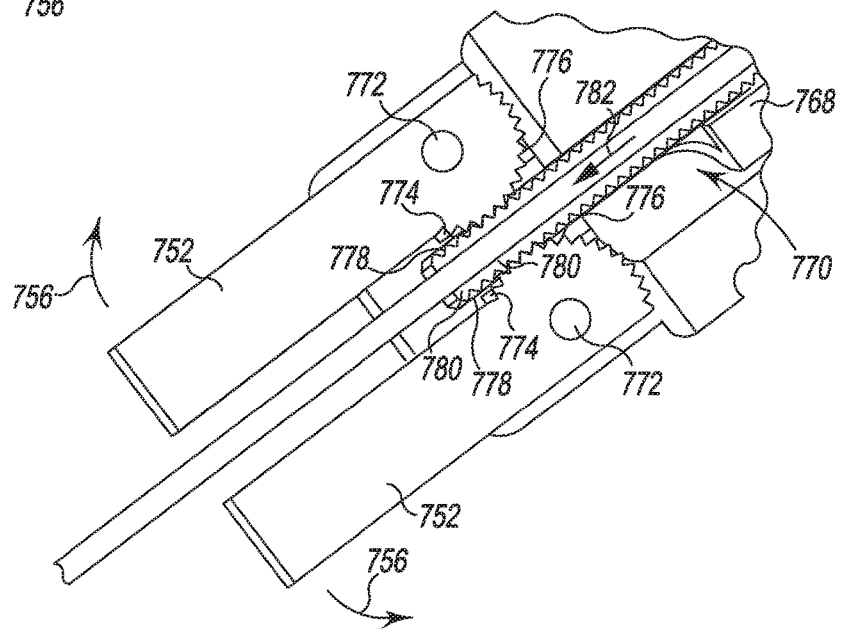
FIG. 22 is a cross-sectional perspective view illustrating a detail of the distal tip of the insertion tool of FIG. 21.
Figure 23:
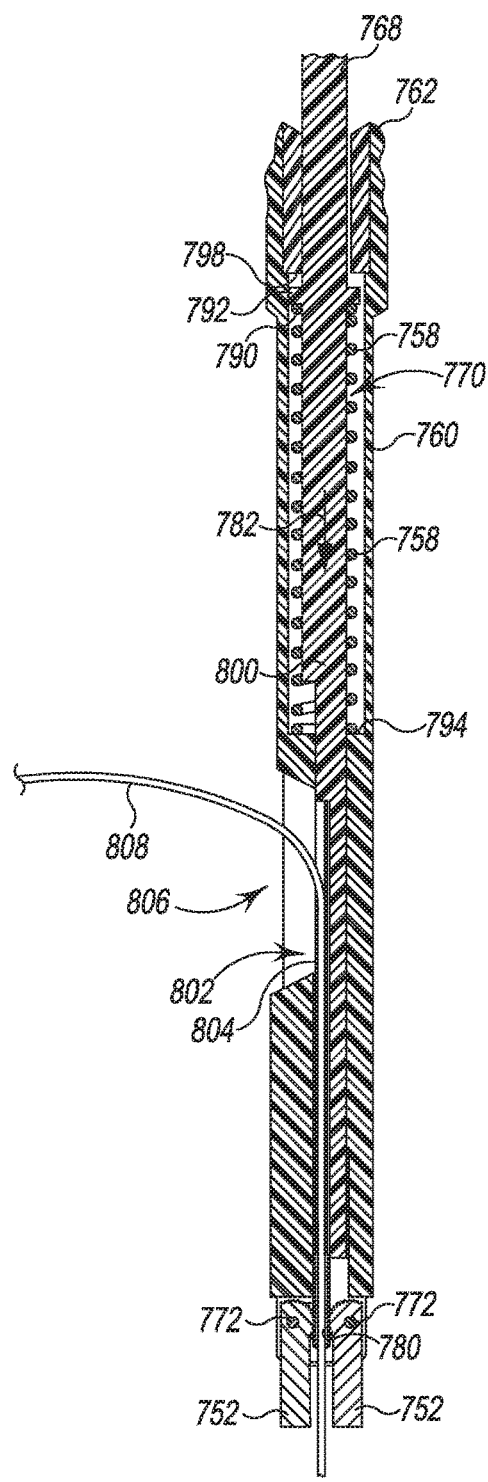
FIG. 23 is a partial cross-sectional plan view taken along the line 23-23 illustrating the insertion tool of FIG. 21.

Referring now to FIGS. 21-23, another embodiment of an insertion tool (hereinafter insertion tool 750) for use with any of the embodiments described above is illustrated. The insertion tool 750 includes a pair of ferromagnetic elements 752. In the illustrative embodiment, each ferromagnetic element 752 is formed as a magnet. In other embodiments, each ferromagnetic element may be formed from, for example, as ferromagnetic stainless steel.

In the illustrative embodiment, the magnets 752 are hinged at the distal tip 754 of the insertion tool 750. Similar to the insertion tool 750, the magnets 752 may fold over in the direction indicated by arrows 756 in FIGS. 21 and 22 to meet the magnets 50, 150, 450 or ferromagnetic materials 250, 350, 534 in the wings or flanges of the prosthesis devices 20, 120, 220, 320, 420, 520 when the wings or flanges are in the deployed or use orientation such that the wings or flanges can be pulled into the un-deployed position. The insertion tool 750 further includes a return spring 758 (see FIG. 23), which biases the magnets 752 in the center position shown in FIG. 21, and returns the magnets 752 to their center position.

As shown in FIG. 21, the insertion tool 750 has an elongated shaft 760 that extends from the distal tip 754 to a proximal end 762 and defines a longitudinal axis 764 of the insertion tool 750. A handle 766 extends outwardly from the proximal end 762 to provide a grip for use in manipulating the insertion tool 750 (and hence the prosthesis device) during operation. The insertion tool 750 also includes an actuator rod 768 that extends outwardly from a passageway 770 (see FIG. 22) defined in the elongated shaft 760. In the illustrative embodiment, the handle 766, the elongated shaft 760, and the actuator rod 768 are formed from hard plastic materials as separate components that are later assembled with the magnets 752 and the spring 758 to form the insertion tool 750.

As shown in FIG. 22, each magnet 752 is hinged to the elongated shaft 760 via a pivot pin 772 that extends through the shaft 760 and each magnet 752. Each magnet 752 includes a plurality of gear teeth 774 that are defined on a curved inner surface 776. The gear teeth 774 of the magnets 752 engage corresponding teeth 778 defined on a distal end 780 of the actuator rod 768. When the rod 768 is advanced distally as indicated by arrow 782 in FIG. 22, the engagement between the teeth 774, 778 causes the magnets 752 to fold or deploy outward in the direction indicated by arrows 756.

As described above, the insertion tool 750 includes a return spring 758, which has a proximal end 790 that engages a proximal annular flange 792 of the rod 768, as shown in FIG. 23. The elongated shaft 760 has an inner wall 794 that engages the distal end 796 of the return spring 758. In that way, the spring 758 is configured to bias the rod 768 in a retracted position and, as a result, bias the magnets 752 in the center position shown in FIGS. 21-23. When the rod 768 is advanced distally as indicated by arrow 782 in FIG. 23, the spring 758 is compressed such that when the rod 768 is released, the spring 758 urges the rod 768 to advance proximally and return the magnets 752 to the center position. As shown in FIG. 23, the annular flange 792 is configured to engage a distal inner wall 798 to prevent the rod 768 from traveling in the proximal direction beyond a predetermined distance. Similarly, the rod 768 includes a stop 800 configured to engage the proximal inner wall 794 of the shaft 760 to prevent the rod 768 from traveling in the distal direction beyond a predetermined distance.

As shown in FIGS. 22 and 23, the actuator rod 768 has a channel 802 that extends from a middle opening 804 through its distal end 780. The middle opening 804 is aligned with a slot 806 defined in a sidewall of the elongated shaft 760. The channel 802 and the slot 806 are sized to permit the passage of, for example, a catheter 808 to advance the catheter into the patient's esophagus or other lumen.

Figure 24:
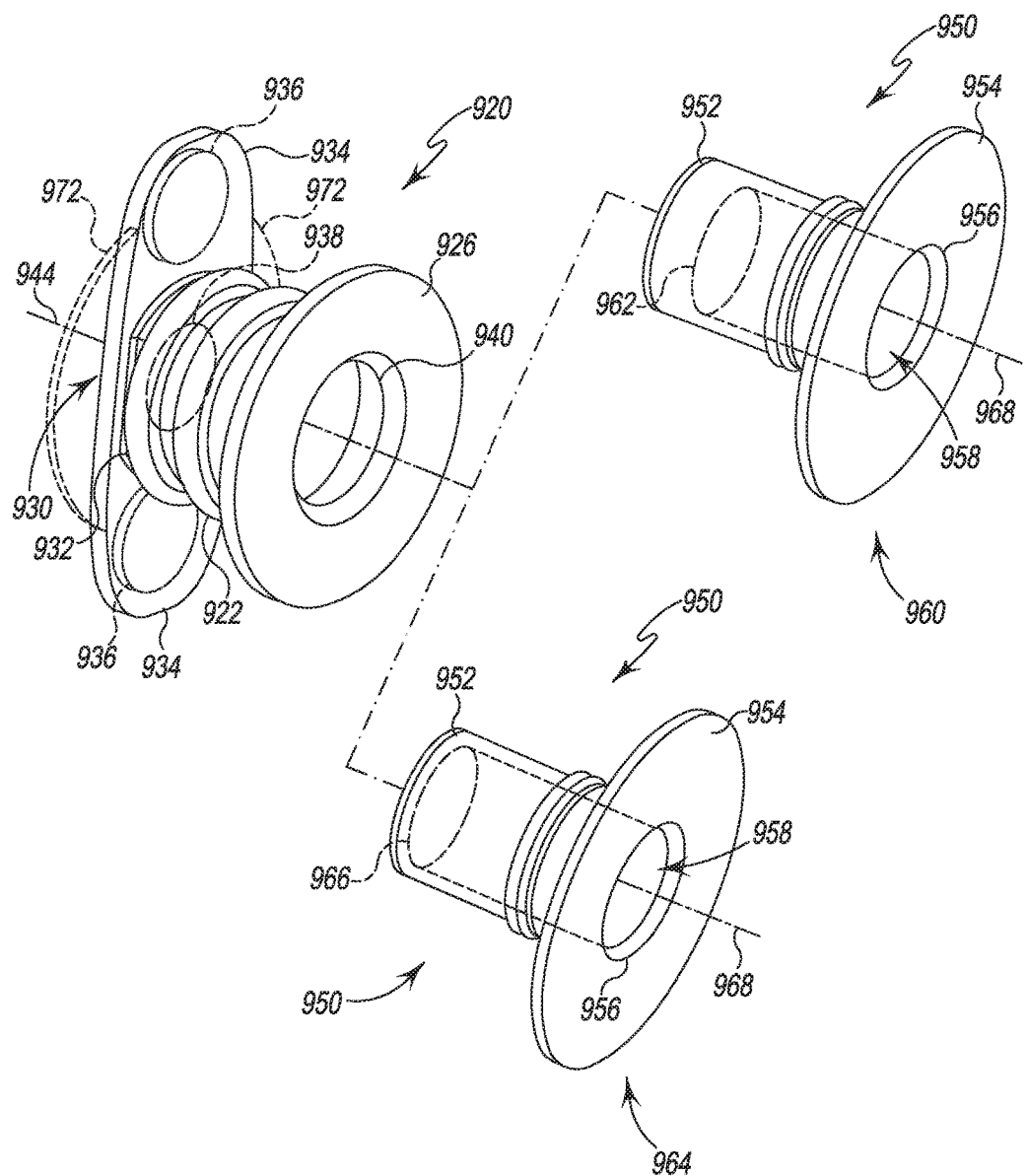
FIG. 24 is a perspective view of another prosthesis system.
Figure 25:
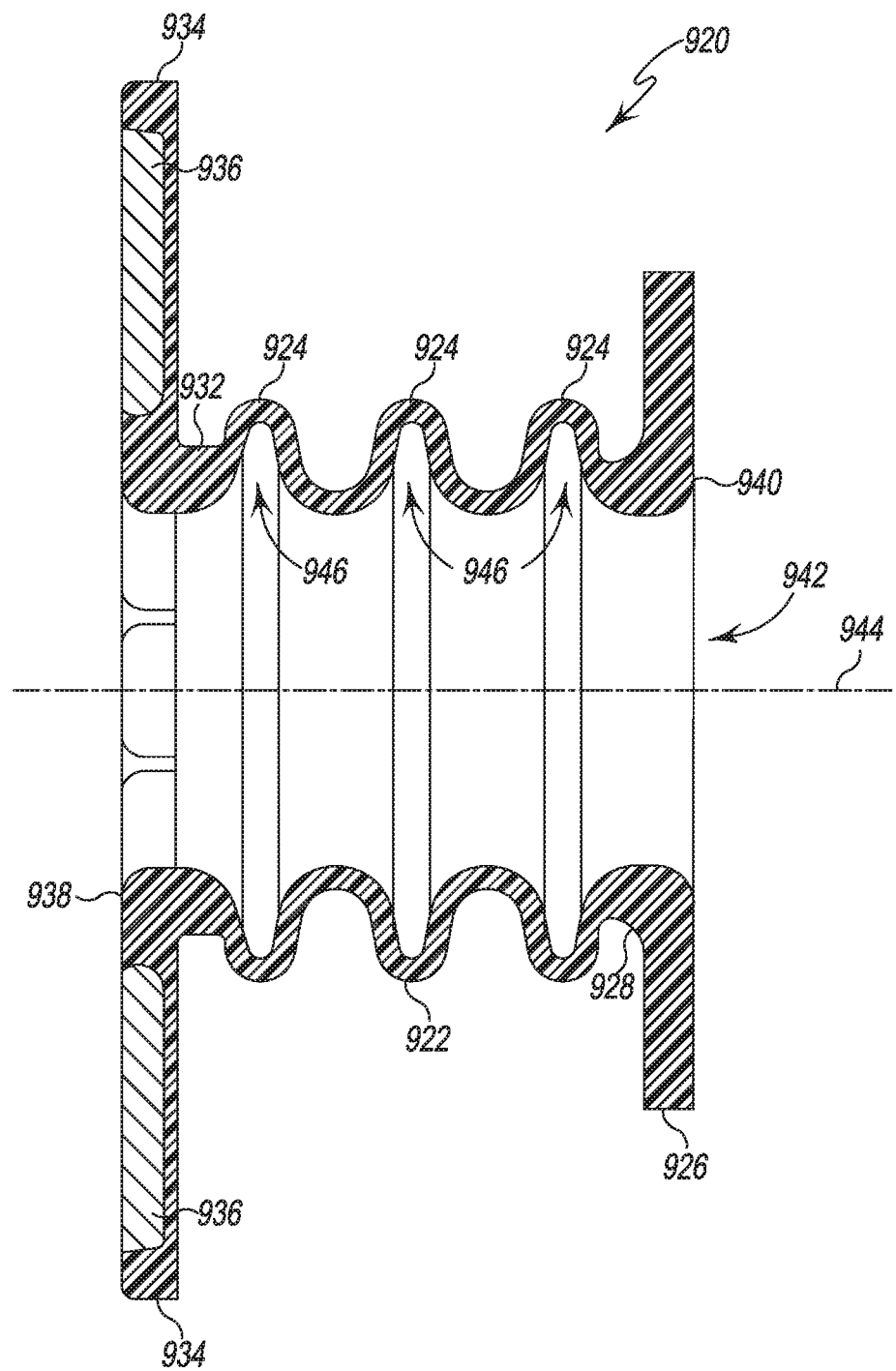
FIG. 25 is a cross-sectional elevation view of a prosthetic device.

Referring now to FIGS. 24-25, another system 910 for use in a surgical procedure is shown. The system 910 includes a prosthesis device 920 that is similar to the devices 20, 120, 220, 320, 420 described above. The system 910 also includes a pair of inserts 950 configured for use with the prosthesis device 920 and may include one of the insertion tools 650, 750 described above. The system 910 may be used, for example, in the treatment of sleep apnea. The device 920 includes a body 922 that is a hollow tube constructed of a biocompatible elastomeric material such as, for example, silicone. The body 922 is sized to be positioned in a tissue puncture, and, in the illustrative embodiment, the body 922 includes a corrugated section 924 to permit the body 922 to increase or decrease in length along its longitudinal axis 944 as necessary during use.

The device 920 includes a flange 926 that extends outwardly from a proximal end 928 of the body 922 and another flange 930 that extends outwardly from an opposite distal end 532. The flange 926 is circular, but it should be appreciated that in other embodiments the flange 926 may be oval, rectangular, or other geometric shape. The flanges 926, 930 are illustratively molded integrally with the body 922. In other embodiments, one or more of the body 922 and the flanges 926, 930 may be formed separately and later assembled. In use, the flange 926 lies at the skin of the patient's neck when the body 922 is positioned in the tissue puncture, while the flange 930 lies along the anterior wall of the patient's trachea.

In the illustrative embodiment, the flange 930 includes a pair of flanges or wings 934 that extend outwardly from the distal end 932 of the body 922. The wings 934 are configured to project in opposite directions along an inner wall of a patient's lumen such as, for example, the anterior wall of a trachea when the device 920 is in a use orientation. When the wings 934 are deployed in the use orientation illustrated in FIGS. 24-25, the wings 934 cooperate with the flange 926 to hold the device 920 in place in the tissue puncture. Each wing 934 includes a ferromagnetic element 936 formed from ferromagnetic stainless steel or the like. In other embodiments, each ferromagnetic element 936 may be a magnet. As shown in FIG. 24, the flange 930 may include one or more base sections 972 that extend outwardly from the distal end 932 of the body 922. The base sections 972 are formed with the wings 934 and illustratively have a thinner material thickness. In such embodiments, the base sections 972 cooperate with the wings 934 to engage the tissue surrounding the distal opening of the tissue puncture and thereby prevent the transmission of fluid from the trachea along the outer surface of the prosthesis device 920.

As shown in FIG. 25, the prosthesis device 920 has a distal opening 938, a proximal opening 940, and a passageway 942 extending along the longitudinal axis 944 that connects the openings 938, 940. The passageway 942 includes a number of annular slots 946 that correspond to the corrugations of the section 924.

As illustrated in FIG. 24, the system 910 includes a pair of inserts 950 configured for use with the prosthesis device 920. Each insert 950 includes an elongated body 952 sized to be positioned in the passageway 942 of the prosthesis device 920 and a proximal flange 954 extending outwardly from the elongated body 952. In the illustrative embodiment, each insert 950 is formed from a biocompatible plastic material and may be transparent or semi-transparent. Each insert 950 also has an opening 956 defined in its proximal end and a passageway 958 that extends inwardly from the opening. One insert 960 has a passageway 958 that extends to a distal base surface 962; the other insert 964 has a passageway 958 that extends to a distal opening 966 and is hence a closed passageway. The flange 954 and elongated body 952 of each insert 950 are sized to cover the proximal opening 940 of the prosthesis device 920. The passageway 958 of each insert 950 extends along the longitudinal axis 968 of the insert 950.

When the insert 960 is used, it may be selectively inserted into the prosthesis device 920 to close the opening 940 to permit the patient to speak and breathe normally. The other insert 964 may be used at other times to permit air to pass directly into the trachea through its distal opening 966, thereby bypassing the throat.

In the illustrative embodiment, each insert 950 includes an annular rib 970 that is sized to be received in one of the annular slots 946 of the prosthesis device 920 to selectively secure the insert 950 to the device 920. In other embodiments, the proximal flange 926 may be provided with magnets and the flange 954 of each insert 950 may comprise ferromagnetic material (or vice versa) so that the insert is attracted by the magnets to secure the insert in position. Each insert may also be provided with a seal or gasket to facilitate the closure of the opening 538.

Prior to insertion of the flange 930 and the wings 934 through the tissue puncture, the insertion tool 750 may be inserted through the body 922 between the wings 934 with the magnets 752 in the orientation shown in FIGS. 21-23. Each wing 934 may be folded such that its respective ferromagnetic element 936 contacts one of the magnets 752 along the centerline 944 of the device 920. To facilitate insertion of the device 920 through tissue puncture, the magnet 752 holds the wings 934 and the flange 930 in this orientation while the wings 934 and the flange 930 are threaded through the tissue puncture into the trachea. A user may then press on the actuator rod 768 as described above to cause the magnets 752 to move to an extended position and permit the wings 934 to deploy into the use orientation shown in FIG. 24. A user may then select one of the inserts 950 for use with the prosthesis device 920.

If it is necessary to remove the device 920 for cleaning, replacement, or the like, the insertion tool 750 may be inserted through the body 922 between the wings 934. A user may then press on the actuator rod 768 as described above to cause the magnets 752 to move to an extended position. The magnets 752 attract the ferromagnetic elements 936 and cause the elements 936 to engage the magnets 752. The user may then release the actuator rod 768, and the return spring 758 urges the rod 768 to advance proximally and return the magnets 752 to the center position, thereby causing the wings 934 to fold along the centerline 944 of the device 920. The user may then remove the device 920.

While the disclosure has been illustrated and described in detail in the drawings and foregoing description, such an illustration and description is to be considered as exemplary and not restrictive in character, it being understood that only illustrative embodiments have been illustrated and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

What is claimed is:

1. A prosthesis system comprising:
   an elastomeric prosthesis device, comprising:
   a body extending from a proximal end to a distal end, the body including a longitudinal axis and a passageway extending through the body along the longitudinal axis, a first flange extending outwardly from the proximal end, a second flange extending from the distal end, the second flange including a planar surface configured to contact soft tissue of a patient, and a pair of ferromagnetic elements attached to the second flange, wherein the second flange is movable relative to the body between a first position in which the pair of ferromagnetic elements are proximate to one another and the longitudinal axis of the body to permit the distal end and the second flange of the elastomeric prosthesis device to be inserted into, and removed from, a patient's soft tissue, and a second position in which the ferromagnetic elements are positioned on opposite sides of the body, and a tool comprising a stem and a pair of magnets pivotally coupled to the stem, the pair of magnets being movable between an un-deployed position in which the magnets are positioned proximate to one another to permit the tool to be inserted through the passageway of the elastomeric prosthesis device and a deployed position in which each magnet is configured to meet a corresponding ferromagnetic element of the second flange when the second flange is in the second position, wherein the magnets of the insertion tool are configured to attract the ferromagnetic elements to cause the second flange to move from the second position to the first position when the magnets are moved from the deployed position to the un-deployed position to permit removal of the elastomeric prosthesis device from the patient's soft tissue.

2. The prosthesis system of claim 1, wherein each ferromagnetic element is a magnet.

3. The prosthesis system of claim 2, wherein the magnets cooperate to hold the second flange in the first position.

4. The prosthesis system of claim 1, wherein the body comprises a corrugated tube.

5. The prosthesis system of claim 1, wherein the second flange includes a pair of wings that project in opposite directions from the body when in the second position, and one of the pair of ferromagnetic elements is attached to each wing.

6. The prosthesis system of claim 5, wherein each wing extends from a base attached to the body to an outer tip, and one of the pair of ferromagnetic elements is attached to the outer tip of each wing.

* * * * *